(12) United States Patent  (10) Patent No.: US 9,283,346 B2
Taylor et al.  (45) Date of Patent: Mar. 15, 2016

(54) PERSONAL USE OXYGEN CONCENTRATOR WITH INTEGRATED FIRE SAFETY

(71) Applicants: Brenton Alan Taylor, Kenwood, CA (US); Peter Hansen, Santa Barbara, CA (US); Daniel Wayne Chin, Goleta, CA (US); Michael Pollack, Goleta, CA (US); Cristian Goebner, Santa Barbara, CA (US)

(72) Inventors: Brenton Alan Taylor, Kenwood, CA (US); Peter Hansen, Santa Barbara, CA (US); Daniel Wayne Chin, Goleta, CA (US); Michael Pollack, Goleta, CA (US); Cristian Goebner, Santa Barbara, CA (US)

(73) Assignee: Inogen, Inc., Goleta, CA (US)

( * ) Notice: Subject to any disclaimer, the term of this patent is extended or adjusted under 35 U.S.C. 154(b) by 0 days.

(21) Appl. No.: 14/341,801

(22) Filed: Jul. 26, 2014

(65) Prior Publication Data
US 2016/0022950 A1 Jan. 28, 2016

(51) Int. Cl.
*B01D 53/02* (2006.01)
*A61M 16/10* (2006.01)
*B01D 53/047* (2006.01)

(52) U.S. Cl.
CPC .......... *A61M 16/101* (2014.02); *B01D 53/047* (2013.01); *B01D 53/0476* (2013.01); *A61M 2016/102* (2013.01); *B01D 2256/12* (2013.01); *B01D 2257/102* (2013.01); *B01D 2259/40009* (2013.01); *B01D 2259/4533* (2013.01)

(58) Field of Classification Search
CPC .......... B01D 53/053; B01D 2253/108; B01D 2256/12; B01D 2257/102; A61M 16/101
See application file for complete search history.

(56) References Cited

U.S. PATENT DOCUMENTS

| | | | |
|---|---|---|---|
| 2004/0112211 A1* | 6/2004 | Meirav | 95/8 |
| 2005/0103341 A1* | 5/2005 | Deane et al. | 128/204.26 |
| 2005/0160909 A1* | 7/2005 | Meirav | 96/108 |
| 2005/0188853 A1* | 9/2005 | Scannell, Jr. | 96/417 |
| 2006/0154642 A1* | 7/2006 | Scannell, Jr. | 455/404.1 |
| 2008/0168798 A1* | 7/2008 | Kotliar | 62/640 |
| 2009/0288662 A1* | 11/2009 | Radford et al. | 128/205.24 |
| 2010/0300708 A1* | 12/2010 | Raphael et al. | 169/54 |
| 2013/0346089 A1* | 12/2013 | Margon | 705/2 |

* cited by examiner

*Primary Examiner* — Christopher P Jones
(74) *Attorney, Agent, or Firm* — Mark Rodgers

(57) ABSTRACT

A personal use oxygen concentrator, including; a controllable user interface including at least one of visual and audio indicators, a power supply, a housing, a controllable product gas output device, a blower, a compressor, a selective adsorption system comprising adsorption beds and gas flow control valves comprising at least one of a PSA, VPSA, or VSA oxygen producing system, a programmable controller configured to control at least one of the blower, compressor, output device, user interface, and selective adsorption system, and an integrated smoke detection system and smoke detector controller, mounted within the housing, configured to be controlled by and provide data to the programmable controller, and the programmable controller may perform predetermined control actions when smoke is detected.

12 Claims, 4 Drawing Sheets

PERSONAL USE OXYGEN CONCENTRATOR WITH INTEGRATED FIRE SAFETY

BACKGROUND

The specification relates to oxygen concentrators for personal use and in particular an oxygen concentrator that includes provision to improve user safety in the event of fire.

Oxygen concentrators for providing oxygen rich air for therapeutic purposes are increasingly popular as alternatives to liquid oxygen vessels and compressed gas cylinders. Such personal oxygen concentrators exist in both portable form for ambulatory use and are relatively small—compared to industrial concentrators—stationary devices for home or other stationary use. Since oxygen concentrators deliver oxygen rich air to the environment and the user, fire prevention and fire safety are considerations when designing, regulating, and utilizing oxygen equipment.

BRIEF DESCRIPTION

In some embodiments, a personal use oxygen concentrator may be provided which improves safety in the event of fire or impending fire by including a controllable smoke detector, integrated with the concentrator, which allows for a level of protective measures and/or alarm indications to be initiated by the concentrator.

In some embodiments a personal use oxygen concentrator may be provided, including; a controllable user interface including at least one of visual and audio indicators, a power supply, a housing, a controllable product gas output device, a blower, a compressor, a selective adsorption system comprising adsorption beds and gas flow control valves comprising at least one of a PSA, VPSA, or VSA oxygen producing system, a programmable controller configured to control at least one of the blower, compressor, output device, user interface, and selective adsorption system, and an integrated smoke detector and smoke detector controller, mounted within the housing, which in some embodiments may be configured to be controlled by and provide data to the programmable controller, indicative of level of smoke concentration detected. Depending on the presence or in some embodiments the level, of smoke concentration detected by the smoke detector, the programmable controller may perform predetermined control actions.

In some embodiments the smoke detector and smoke detector controller may be mounted on a PCB within the concentrator housing. In some embodiments the concentrator may also include a controllable power supply.

In some embodiments the smoke detector may be at least one of a photoelectric detector or a photo-ionic detector.

In some embodiments the smoke detector and smoke detector controller may be configured to continually sample and report to the programmable controller.

In some embodiments the predetermined control actions may include at least one of; change blower speed, shut off product output, shut down compressor shut down selective adsorption system, sound or display alarm indicators, shut off power supply.

In some embodiments the programmable controller may include a clock and sampled smoke detector data may be logged versus time.

In some embodiments the smoke detector and smoke detector controller may include self-test modes, which may periodically initiated by the controller and the results indicated with the user interface.

In some embodiments the product output may include a metal hose bib.

DETAILED DESCRIPTION OF ILLUSTRATIVE EMBODIMENTS

Figure 1:
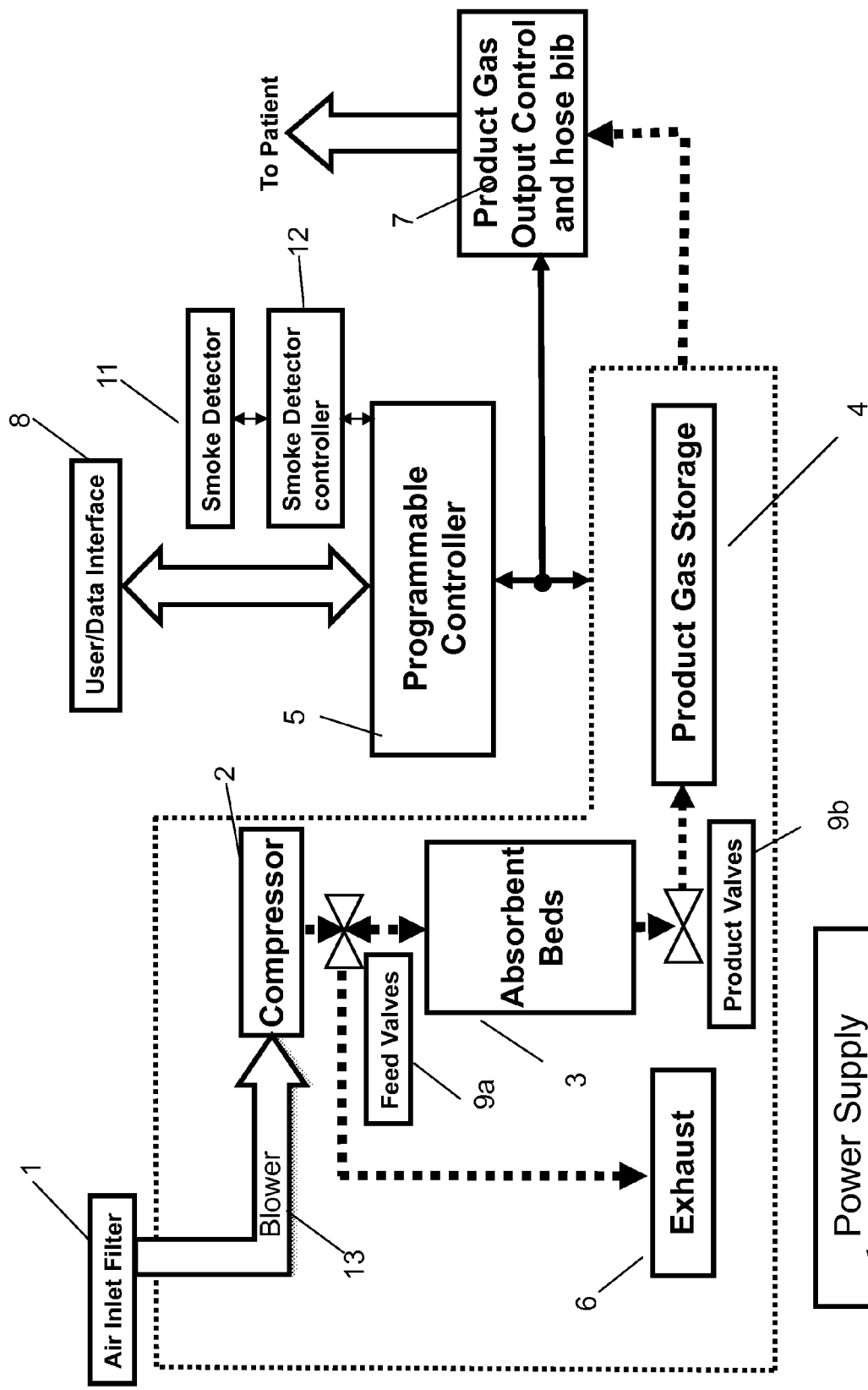
FIG. 1 is a block diagram of an illustrative embodiment of the invention.

One or more embodiments described herein may provide improved safety for personal use oxygen concentrators in the event or vicinity of fire or smoke.

One or more embodiments described herein may provide a record of smoke concentration over time in the vicinity of a personal use oxygen concentrator.

One or more embodiments may provide and/or exceed regulatory fire safety compliance for personal use concentrators.

Personal use therapeutic oxygen concentrators are increasing in popularity, both in very small portable form and relatively small, compared to industrial gas concentrators, stationary home devices. A small stationary personal use concentrator is describe in co-pending application U.S. Ser. No. 14/142,613, assigned to the same assignee of the current application and incorporated in its entirety by reference, and in which the operation and use of such concentrators is described. Such concentrators because of their small size and intended personal use, have differing design considerations from large industrial concentrators intended to produce large quantities of concentrated gasses. For example in an illustrative embodiment, the personal use concentrator may be designed to produce product gas in the zero to five liter per minute range and may weigh less than 55 pounds, as opposed to industrial concentrators which may be orders of magnitude larger in size and capacity.

Referring to Figure an illustrative embodiment is shown. Concentrator elements may include a blower 2, which draws in air through an inlet filter 1. Some of the air may be directed over the concentrator components for cooling by blower 13, while a portion may be directed to, or from, compressor 2 which pressurizes, or draws a vacuum or combination of the two. The compressed or vacuum drawn air passes through a selective adsorption system, which may include feed and product valves 9a and 9b and adsorbent beds 3. Valves in conjunction with adsorbent beds may plumbed and actuated to form the selective adsorption system based on VSA, PSA, VPSA, or other pressure swing adsorption techniques. Pressurized product gas may be optionally stored 4 and the oxygen rich product is delivered to the patient through a suitable product gas output device 7. The concentrator may be powered by a power source, either battery, AC, AC-DC, or some combination.

In some embodiments, the concentrator includes an intelligent programmable controller 5. The concentrator elements described may be configured to be controllable by the concentrator. For instance the blower speed and on/off state, compressor speed and on/off state, all valve timing, product gas output, power supply on/off, and a variety of sensors not shown such as pressure, oxygen concentration, temperature and others arranged in the concentrator—some or all may be designed to be read and controlled by the controller in various embodiments, depending on the level of control desired. A concentrator arranged thusly may be capable of a wide range of fine control, adjustment and maintenance operations as described in the incorporated reference. Additionally a user interface 8 may be present including a combination of visual and audio display and indicators, also under controller direction.

Also shown in the illustrative embodiment of FIG. 1 is integrated smoke detector 11 and smoke detector controller 12 which form a smoke detection system. Due to the presence of oxygen rich air at a concentrator, regulatory requirements dictate that such personal use concentrators include some provision to stop the flow of oxygen in the event of a fire burning in the oxygen tubing.

Smoke detector 11 may be advantageously selected to mount to the concentrator to ensure that its function is always at hand during concentrator use. Smoke detectors suitable for such use include small photoelectric and photo-ionic detectors that come in sizes on the order of a few inches or less in diameter, or on a side, and may be PCB mountable. Such detectors may include or contain their own controllers, which in some cases include the ability to detect and communicate various levels of contamination. Smoke detection systems will provide an alarm signal based on detecting the presence of smoke, which depending on type of system, may range from a simple concentration threshold exceeded, signals indicative of more than one concentration threshold, or continuous concentration information. Such smoke detection systems mated with a concentrator under programmable control may provide benefit beyond the simple alarming due to detecting a predetermined smoke concentration or alarm output from the smoke detection controller. However, an alarm coupled with a shut-off off of the oxygen production in the presence of a dangerous smoke concentration may in and of itself be an advantageous result, and such a configuration may be useful both for regulatory compliance and improved safety since the flow of oxygen can be stopped before the fire reaches physical fire breaks in the oxygen tubing or concentrator hose bib.

Given the ability to determine a range of smoke concentrations, however, a range of actions by the controller may be taken. Predetermined levels could trigger increasingly serious measures as detected smoke levels increase, particularly for a concentrator controller that can perform a variety of control functions. For instance, low levels of smoke could trigger increased or decreased blower speed to either flush out residual smoke if a transient condition is encountered or accelerate the sampling rate to detect a dangerous condition as quickly as possible. At higher smoke levels a variety of actions could take place. Some predetermined levels may trigger shutting down the output device, others may include shutting down oxygen production, either by compressor shutdown and/or valve shut down in the selective adsorption section. Other levels may trigger powering off the concentrator. Each action may include audio and/or visual indicators through the user interface. However even for smoke detection systems with limited concentration threshold information, the levels of predetermined action could be triggered by the frequency of smoke alarm events. Regardless of the level of sophistication of the smoke detection system, an intelligent controller sampling the smoke detector system outputs can provide for intelligent and measured response.

The combination of a smart smoke detection system and smart concentrator controller may also produce advantageous results over time beyond the actions in response to a particular event. If the concentrator controller includes clock functions, it may continuously sample the smoke detector at selected intervals to log the presence and/or concentration of particles in the air over time. Such capability may lead to direct action, such as changing blower speed and to maintenance benefits such as indicating the need to change air filters or other cleaning operations. In the event of a fire or smoke related accident involving the concentrator, data logging may provide valuable historical data.

Figure 3:
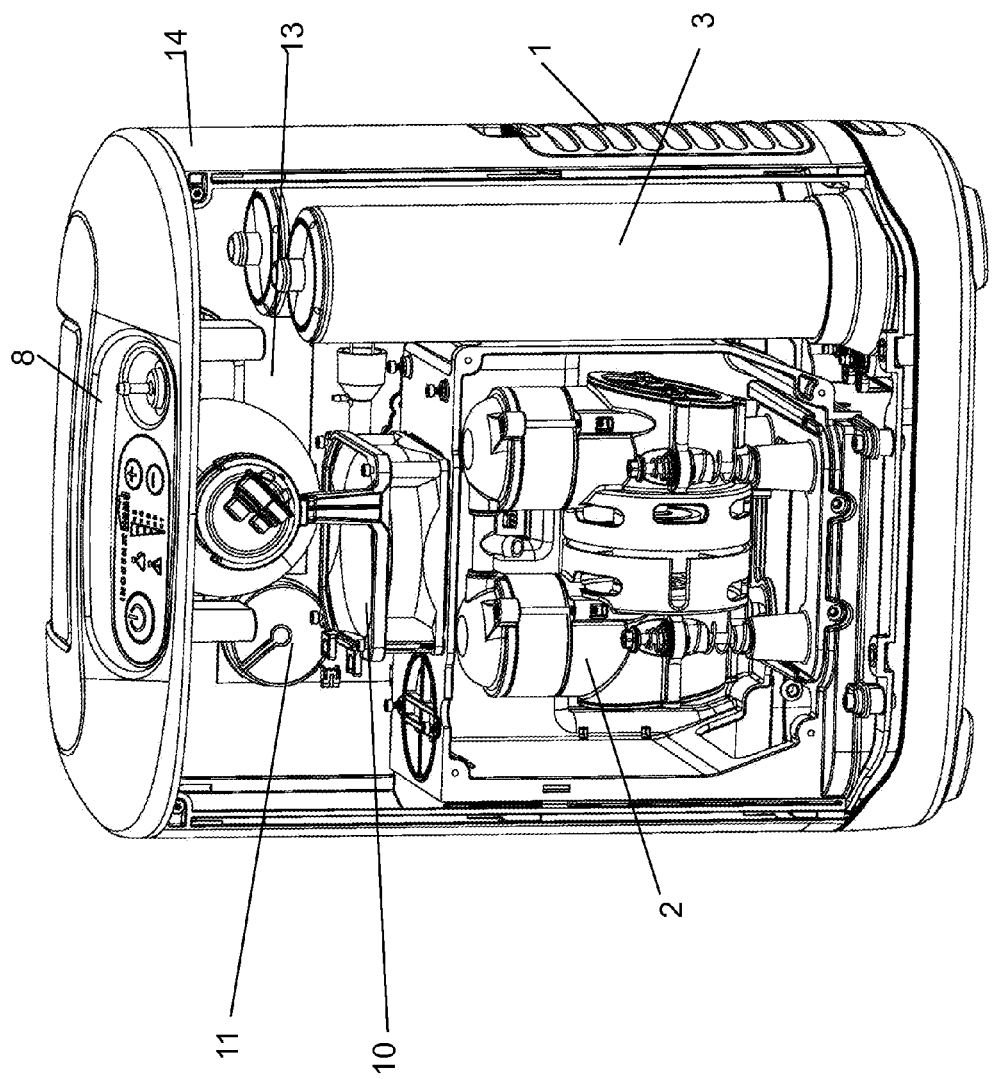
FIG. 3 shows a concentrator with smoke detector, according to an illustrative embodiment.

The smoke detector functionality may be combined with a fire-resistant metal hose bib 15 shown in FIG. 3 as part of the product output device and overall fire safety system.

Figure 2:
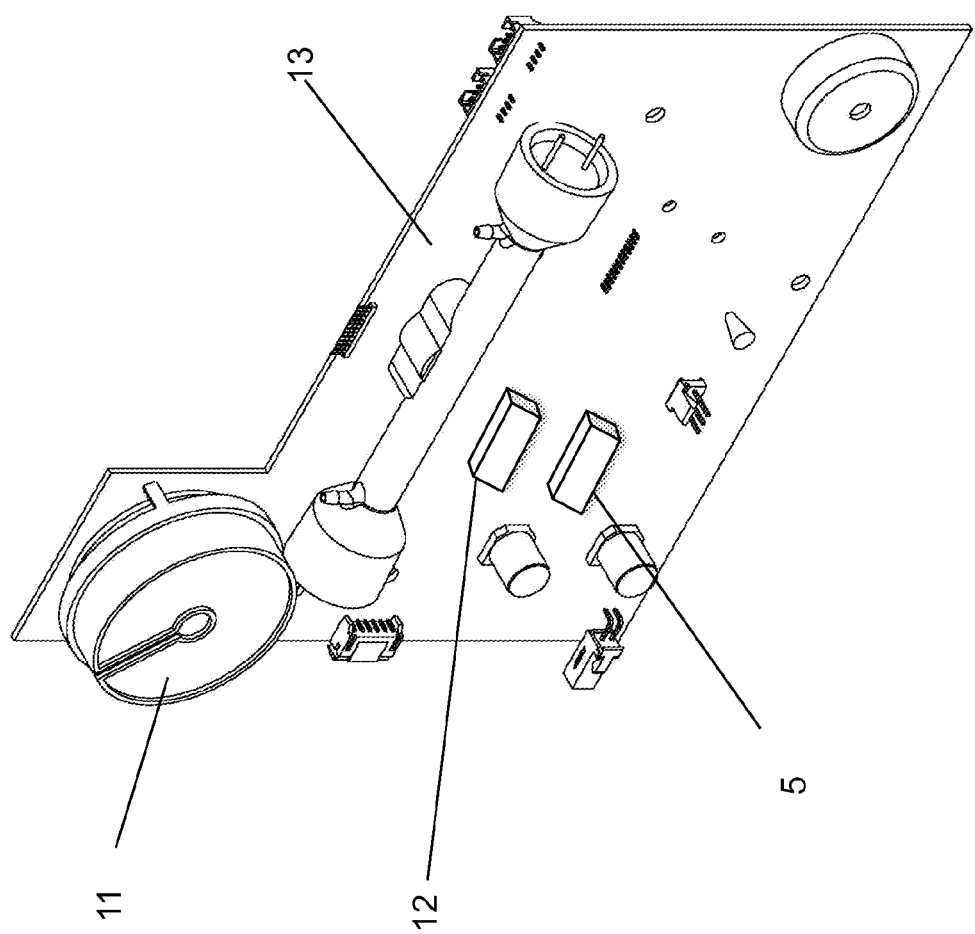
FIG. 2 is an illustrative embodiment of an integrated smoke detector.

FIG. 2 depicts an illustrative example of integrating a smoke detection system with a concentrator. PCB 13 may already be present in a concentrator and may include the programmable controller 5 as well as other system electronics and sensors. Such a PCB 13 may be modified to include PCB mountable smoke chamber 11 and smoke detector controller 12, if the controller is separate from the smoke chamber itself.

FIG. 3 shows an illustrative example of the embodiment of FIG. 2 integrated with an exemplary concentrator. Concentrator housing 14 houses the components and contains internal airflow. Blower 10 draws air through inlet filter 1 over the components and to compressor 2 which compresses air and delivers it to adsorbent beds 3. PCB 13 includes smoke detector 11. User interface 8 provides user control and display.

Figure 4:
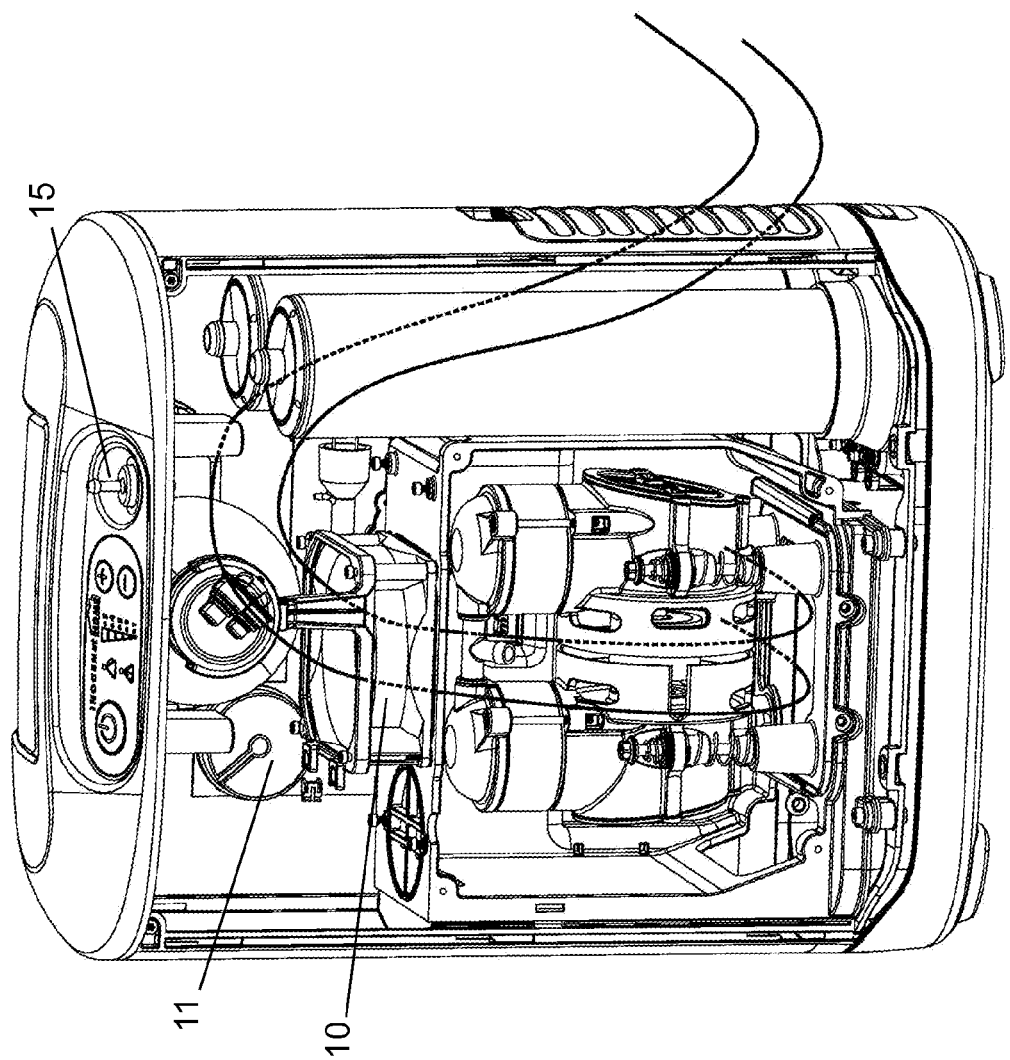
FIG. 4 shows air flow in the concentrator of FIG. 3, according to an illustrative embodiment.

FIG. 4 illustrates airflow drawn in by blower 10 and directed over the vicinity of smoke detector 11 to ensure adequate sampling of the ambient air for smoke.

The embodiments described herein are exemplary. Modifications, rearrangements, substitute devices, etc. may be made to these embodiments and still be encompassed within the teachings set forth herein.

The invention claimed is:

1. A personal use oxygen concentrator, comprising;
   a. a controllable user interface including at least one of visual and audio indicators,
   b. a housing,
   c. a product gas output device,
   d. a blower,
   e. a compressor,
   f. a selective adsorption system comprising adsorption beds and gas flow control valves comprising at least one of a PSA, VPSA, or VSA oxygen producing system
   g. a programmable controller configured to control at least one of the blower, compressor, output device, user interface, and selective adsorption system and;
   h. an integrated smoke detector and smoke detector controller, mounted within the housing, configured to indicate the presence of smoke within the concentrator housing and patient delivery tubing and fixtures, wherein the smoke detector samples air drawn into the housing by the blower at a higher flow rate than ambient air and the programmable controller will perform predetermined control actions when the presence of smoke is detected.

2. The concentrator of claim 1 further comprising a controllable power supply.

3. The concentrator of claim 1 wherein the smoke detector is configured to be controlled by and provide data to the programmable controller.

4. The concentrator of claim 1 wherein the predetermined actions taken by the controller depend on the level of smoke concentration detected by the smoke detector.

5. The concentrator of claim 1, wherein the smoke detector and smoke detector controller are mounted on a PCB within the concentrator housing.

6. The concentrator of claim 1, wherein the smoke detector is at least one of a photoelectric detector or a photo-ionic detector.

7. The concentrator of claim 3, wherein the smoke detector and smoke detector controller are configured to continually sample and report to the programmable controller.

8. The concentrator of claim 1, wherein the predetermined control actions include at least one of;
   a. change blower speed,
   b. shut off product output,
   c. shut down compressor
   d. shut down selective adsorption system,
   e. sound or display alarm indicators,
   f. shut off power supply.

9. The concentrator of claim 4, wherein the programmable controller comprises a clock and sampled smoke detector data is logged versus time.

10. The oxygen concentrator of claim 1, wherein the smoke detector and smoke detector controller include self-test modes which are periodically initiated by the controller and the results indicated with the user interface.

11. The concentrator of claim 1 wherein the concentrator output is controlled within 0 and 5 liters per minute and the concentrator weight is less than 55 pounds.

12. The oxygen concentrator of claim 1 wherein the product output includes a metal hose bib.

* * * * *